(12) United States Patent
Abele et al.

(10) Patent No.: US 9,422,249 B2
(45) Date of Patent: Aug. 23, 2016

(54) PREPARATION OF PYRIMIDINE INTERMEDIATES USEFUL FOR THE MANUFACTURE OF MACITENTAN

(71) Applicant: ACTELION PHARMACEUTICALS LTD., Allschwil (CH)

(72) Inventors: Stefan Abele, Allschwil (CH);
Jacques-Alexis Funel, Allschwil (CH);
Ivan Schindelholz, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/780,383

(22) PCT Filed: Mar. 26, 2014

(86) PCT No.: PCT/IB2014/060160
§ 371 (c)(1),
(2) Date: Sep. 25, 2015

(87) PCT Pub. No.: WO2014/155304
PCT Pub. Date: Oct. 2, 2014

(65) Prior Publication Data
US 2016/0052891 A1    Feb. 25, 2016

(30) Foreign Application Priority Data

Mar. 27, 2013 (EP) .................................... 13161422

(51) Int. Cl.
*C07D 239/47*    (2006.01)
(52) U.S. Cl.
CPC ................................... *C07D 239/47* (2013.01)
(58) Field of Classification Search
CPC .................................................... C07D 239/47
See application file for complete search history.

(56) References Cited

U.S. PATENT DOCUMENTS 6,136,971 A    10/2000    Harrington

FOREIGN PATENT DOCUMENTS

WO    WO 02/053557    *    7/2002     ............ C07D 401/04
WO    WO 2006/051502         5/2006

OTHER PUBLICATIONS

Bolli, et al; "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist"; Journal of Medicinal Chemistry, 55(17); pp. 7849-7861; 2012.
Harrington, et al.; "Research and Development of a Second-Generation Process for Bosentan, an Endothelin Receptor Antagonist"; Organic Process Research & Development; vol. 6; pp. 120-124; 2002.
Schlessinger, et al.; "Total Synthesis of Racemic Verrucarol"; J. Am. Chem. Soc.; vol. 104; pp. 1116-1118; 1982.

* cited by examiner

*Primary Examiner* — Erich A Leeser
(74) *Attorney, Agent, or Firm* — Hoxie & Associates LLC

(57) ABSTRACT

The present invention relates to a new synthetic intermediate, namely the compound of formula I-2

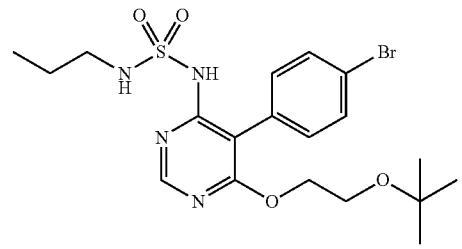

or a salt thereof. Said compound of formula I-2 or its salt can be used to prepare the compound of formula I-3

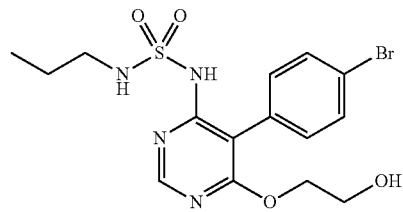

which is an important synthetic intermediate used in the preparation of macitentan.

15 Claims, No Drawings

PREPARATION OF PYRIMIDINE INTERMEDIATES USEFUL FOR THE MANUFACTURE OF MACITENTAN

CROSS REFERENCE TO RELATED APPLICATIONS

This application is a United States Application under 35 U.S.C. 371 claiming benefit of PCT Application No. PCT/IB2014/060160, filed on Mar. 26, 2014, which claims the benefit of European Patent Application No. 13161422.4, filed on Mar. 27, 2013, the contents of each of which are incorporated herein by reference.

The present invention relates to a new synthetic intermediate, namely the compound of formula I-2

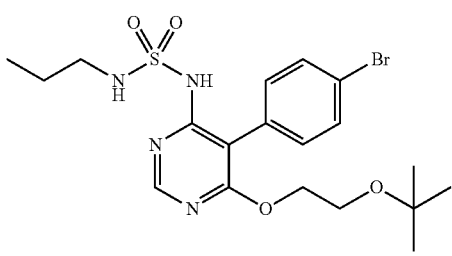

or a salt thereof. Said compound of formula I-2 or its salt can be used to prepare the compound of formula I-3

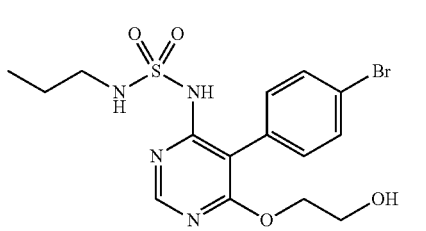

which is an important synthetic intermediate used in the preparation of macitentan. The invention furthermore relates to a method for preparing the compound of formula I-2, to a process for manufacturing the compound of formula I-3 starting from the compound of formula I-2 and to the use of the compound of formula I-2 in a process for manufacturing the compound of formula I-3.

Macitentan (chemical names: N-[5-(4-bromophenyl)-6-[2-[(5-bromo-2-pyrimidinyl)oxy]ethoxy]-4-pyrimidinyl]-N'-propylsulfamide or N-[5-(4-bromophenyl)-6-{2-[(5-bromopyrimidin-2-yl)oxy]ethoxy}pyrimidin-4-yl]-N'-propyl sulfuric diamide) is an endothelin receptor antagonist that has notably been approved by the US Food and Drug Administration and the European Commission for the treatment of pulmonary arterial hypertension. The last step of its two potential preparation routes described in WO 02/053557, called "Possibility A" and "Possibility B", can be summarised as shown in Scheme A1 hereafter.

Scheme A1

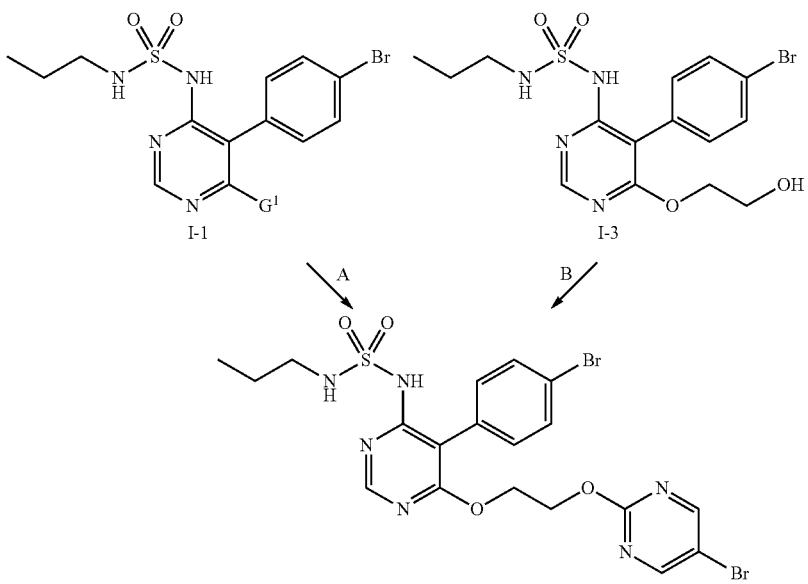

In Scheme A1, $G^1$ represents a reactive residue, and preferentially a chloro atom.

The preparation of macitentan according to "Possibility B" of WO 02/053557 has furthermore been described in Bolli et al., *J. Med. Chem.* (2012), 55, 7849-7861. Accordingly:

KOtBu was added to a solution of ethylene glycol in dimethoxyethane and the compound of formula I-1 wherein $G^1$ is Cl (see Scheme A1 above) was added thereto; after heating at 100° C. for 70 h, work-up involving extraction and purification by column chromatography, the compound of formula I-3 was obtained in a 86% yield; and The compound of formula I-3 was added to a suspension of NaH in THF, the mixture was stirred and diluted with DMF before 5-bromo-2-chloropyrimidine was added; after heating at 60° C. and work-up involving extraction and crystallisation steps, macitentan was obtained in a 88% yield.

As an alternative to the first step of the method described by Bolli et al., the compound of formula I-1 wherein $G^1$ is Cl could be mixed with an excess of ethylene glycol (about 30-50 equivalents), an excess of tBuOK (3-4 equivalents) could be added and the resulting mixture could be heated to 100° C. After addition of water and MeOH and pH adjustment with HCl, the compound of formula I-3 could then be filtered off and obtained, after drying under vacuum, in an about 85% yield.

The methods for manufacturing macitentan described above are however not appropriate for manufacturing macitentan in a sufficient purity unless numerous purification steps are undertaken to remove the impurities from the compound of formula I-3 before performing the step corresponding to "Possibility B" of WO 02/053557. In this regard, it should be mentioned that ethylene glycol is actually toxic and rather difficult to remove by distillation due to a high boiling point.

Noteworthingly, 2-(tert-butoxy)ethanol has been used in a manufacturing process for obtaining bosentan disclosed in U.S. Pat. No. 6,136,971 and in Harrington et al., *Org. Process Res. Dev.* (2002), 6, 120-124. The last steps of said manufacturing process can be summarised as shown in Scheme A2 hereafter.

Scheme A2

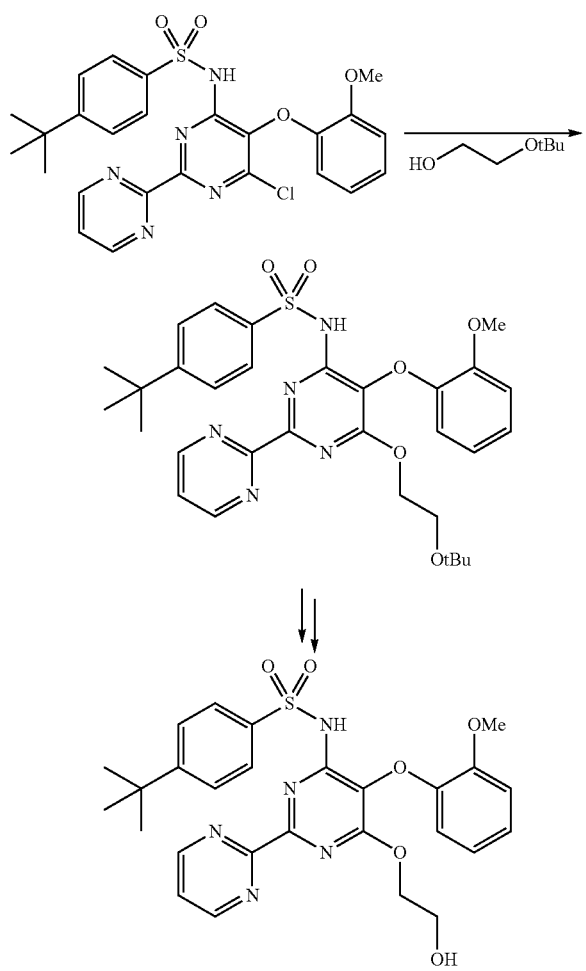

According to the process of U.S. Pat. No. 6,136,971 and Harrington et al., formic acid is used to remove the tent-butyl group in the last steps leading to bosentan with isolation of an additional intermediate, i.e. the O-formylated intermediate.

However the process of Harrington et al., *Org. Process Res. Dev.* (2002), 6, 120-124 could not work with the compound of formula I-2 due to the presence of the more fragile sulfamide group instead of the sulfonamide group in the precursor of bosentan. Actually, an undesired side reaction occurs wherein said sulfamide group is cleaved to leave the amino group on the pyrimidine core (see Scheme 1 hereafter).

Scheme 1

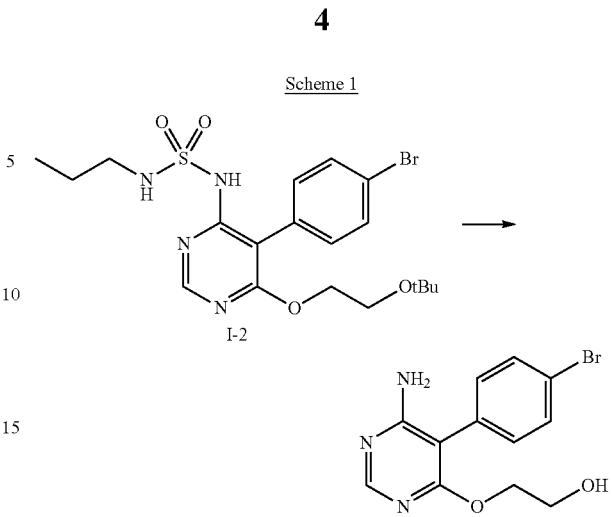

Many further attempts to remove selectively the tert-butyl group were performed, using aqueous mineral acids (such as HCl or $H_2SO_4$) or Lewis acids (such as $AlCl_3$, $BF_3.OEt_2$, $FeCl_3$, $BCl_3$, $Et_2AlCl$, $EtAlCl_2$, TMSI, TMSCl, $Tf_2O$ or TBSOTf); however they all provided either no reaction (with some degradation) or low to moderate conversion. Surprisingly however, it was found that $TiCl_4$, a Lewis acid which may also be used to cleave tert-butyl ether groups (Schlessinger and Nugent, *J. Am. Chem. Soc.* (1982), 104, 1116-1118), allowed complete removal of the tert-butyl group from the compound of formula I-2 without harming the sulfamide group.

It has thus now been found that a new manufacturing route was possible wherein the compound of formula I-1 wherein $G^1$ is Cl is reacted with 2-(tert-butoxy)ethanol to yield a new synthetic intermediate, namely the compound of formula I-2, and said compound of formula I-2 is selectively deprotected to yield the compound of formula I-3. This new manufacturing route provides the compound of formula I-3 in a high purity without extensive purification steps (a simple filtration being sufficient). As a result, said new manufacturing route also allows to obtain macitentan from the compound of formula I-3 in high purity without requiring extensive purification steps.

Various embodiments of the invention are presented hereafter:

1) The invention firstly relates to the compound of formula I-2

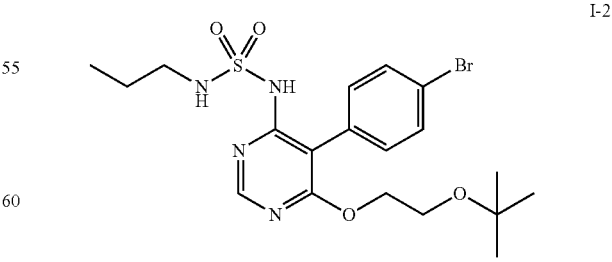

or a salt thereof.

2) The invention also relates to a process for manufacturing the compound of formula I-2 as defined in embodiment 1), said process comprising the reaction of the compound of formula I-1

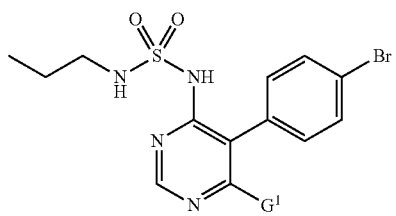

wherein $G^1$ represents halogen, or a salt of said compound, with 2-(tert-butoxy)ethanol in the presence of a base at a temperature from 25 to 140° C.

3) Preferably, the compound of formula I-1 used in the process according to embodiment 2) will be such that $G^1$ represents chlorine.

4) Preferably also, the base used in the process according to embodiment 2) or 3) will be selected from the group consisting of NaOH, KOH and potassium tert-butylate.

5) Preferably also, in the process according to any of embodiments 2) to 4), the reaction of the compound of formula I-1 with 2-(tert-butoxy)ethanol will be performed at a temperature from 40 to 140° C., and in particular at a temperature from 50 to 95° C.

6) More preferably, in the process according to any of embodiments 2) to 4), the reaction of the compound of formula I-1 with 2-(tert-butoxy)ethanol will be performed at a temperature from 70 to 95° C., and in particular at a temperature of about 85° C.

7) In particular, the process according to embodiment 2) will comprise the reaction of the compound of formula I-1 wherein $G^1$ represents chlorine, or a salt thereof, with 2-(tert-butoxy)ethanol in the presence of a base selected from the group consisting of NaOH and potassium tert-butylate at a temperature from 70 to 95° C. (and in particular at a temperature of about 85° C.).

8) Preferably, in the process according to any of embodiments 2) to 7), the reaction of the compound of formula I-1 with 2-(tert-butoxy)ethanol will be performed in an aprotic solvent or mixture of solvents.

9) More preferably, in the process according to any of embodiments 2) to 7), the reaction of the compound of formula I-1 with 2-(tert-butoxy)ethanol will be performed in an aprotic solvent or mixture of solvents comprising dichloromethane, toluene, or a mixture of dichloromethane and toluene (and will notably be performed in dichloromethane, toluene or a mixture of dichloromethane and toluene).

10) Even more preferably, in the process according to any of embodiments 2) to 7), the reaction of the compound of formula I-1 with 2-(tert-butoxy)ethanol will be performed in an aprotic solvent or mixture of solvents comprising toluene (and will notably be performed in toluene).

11) In particular, the process according to embodiment 2) will comprise the reaction of the compound of formula I-1, wherein $G^1$ represents chlorine, or a salt thereof, with 2-(tert-butoxy)ethanol in toluene in the presence of a base selected from the group consisting of NaOH and potassium tent-butylate at a temperature from 70 to 95° C. (and in particular at a temperature of about 85° C.).

12) The invention also relates to a process for manufacturing the compound of formula I-3

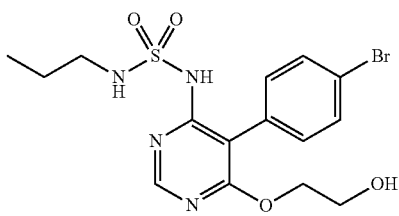

or a salt thereof, said process comprising the reaction of the compound of formula I-2 as defined in embodiment 1), or a salt of said compound, with $TiCl_4$ in an aprotic solvent or mixture of aprotic solvents.

13) Preferably, the aprotic solvent or mixture of aprotic solvents used in the process according to embodiment 12) will comprise toluene, dichloromethane or a mixture of toluene and dichloromethane.

14) More preferably, the reaction of the compound of formula I-2 with $TiCl_4$ in the process according to embodiment 12) will be performed in toluene, dichloromethane or a mixture of toluene and dichloromethane.

15) According to one variant of embodiment 14), the reaction of the compound of formula I-2 with $TiCl_4$ in the process according to embodiment 12) will be performed in toluene.

16) According to another variant of embodiment 14), the reaction of the compound of formula I-2 with $TiCl_4$ in the process according to embodiment 12) will be performed in dichloromethane.

17) According to yet another variant of embodiment 14), the reaction of the compound of formula I-2 with $TiCl_4$ in the process according to embodiment 12) will be performed in a mixture of toluene and dichloromethane.

18) Preferably, the reaction of the compound of formula I-2 with $TiCl_4$ in the process according to any of embodiments 12) to 17) will be performed at a temperature from 0 to 140° C.

19) More preferably, the reaction of the compound of formula I-2 with $TiCl_4$ in the process according to any of embodiments 12) to 17) will be performed at a temperature from 10 to 100° C.

20) In a particularly preferred manner, the reaction of the compound of formula I-2 with $TiCl_4$ in the process according to any of embodiments 12) to 17) will be performed at a temperature from 20 to 70° C.

21) The invention moreover relates to a process for manufacturing a compound of formula I-3

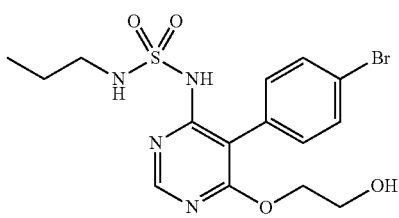

or a salt thereof, said process comprising:

a) the reaction of the compound of formula I-1

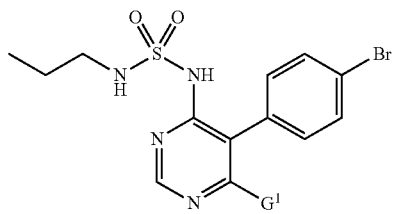

I-1 wherein G¹ represents halogen, or a salt of said compound, with 2-(tert-butoxy)ethanol in the presence of a base at a temperature from 25 to 140° C. to obtain the compound of formula I-2

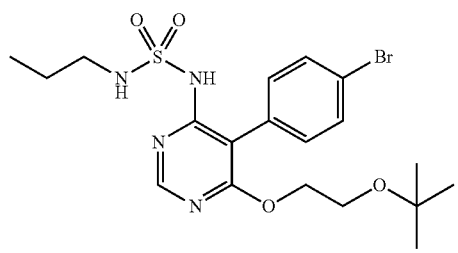

I-2 and b) the reaction of the compound or salt obtained at step a) with $TiCl_4$ in an aprotic solvent or mixture of solvents.

22) Preferably, the compound of formula I-1 used in step a) of the process according to embodiment 21) will be such that G¹ represents chlorine.

23) Preferably also, the base used in step a) of the process according to embodiment 21) or 22) will be selected from the group consisting of NaOH, KOH and potassium tert-butylate.

24) Preferably also, in step a) of the process according to any of embodiments 21) to 23), the reaction of the compound of formula I-1 with 2-(tert-butoxy)ethanol will be performed at a temperature from 40 to 100° C., and in particular at a temperature from 50 to 95° C.

25) More preferably, in step a) of the process according to any of embodiments 21) to 23), the reaction of the compound of formula I-1 with 2-(tert-butoxy)ethanol will be performed at a temperature from 70 to 95° C., and in particular at a temperature of about 85° C.

26) In particular, step a) of the process according to embodiment 21) will comprise the reaction of the compound of formula I-1 wherein G¹ represents chlorine, or a salt thereof, with 2-(tert-butoxy)ethanol in the presence of a base selected from the group consisting of NaOH and potassium tert-butylate at a temperature from 70 to 95° C. (and in particular at a temperature of about 85° C.).

27) Preferably, in step a) of the process according to any of embodiments 21) to 26), the reaction of the compound of formula I-1 with 2-(tert-butoxy)ethanol will be performed in an aprotic solvent or mixture of solvents.

28) More preferably, in step a) of the process according to any of embodiments 21) to 26), the reaction of the compound of formula I-1 with 2-(tert-butoxy)ethanol will be performed in an aprotic solvent or mixture of solvents comprising toluene (and will notably be performed in toluene).

29) In particular, step a) of the process according to embodiment 21) will comprise the reaction of the compound of formula I-1, wherein G¹ represents chlorine, or a salt thereof, with 2-(tert-butoxy)ethanol in toluene in the presence of a base selected from the group consisting of NaOH and potassium tert-butylate at a temperature from 70 to 95° C. (and in particular at a temperature of about 85° C.).

30) Preferably, the aprotic solvent or mixture of aprotic solvents used in step b) of the process according to any of embodiments 21) to 29) will comprise toluene or dichloromethane.

31) More preferably, the reaction of the compound of formula I-2 with $TiCl_4$ in step b) of the process according to any of embodiments 21) to 29) will be performed in toluene, dichloromethane or a mixture thereof.

32) According to one variant of embodiment 31), the reaction of the compound of formula I-2 with $TiCl_4$ in step b) of the process according to any of embodiments 21) to 29) will be performed in toluene.

33) According to another variant of embodiment 31), the reaction of the compound of formula I-2 with $TiCl_4$ in step b) of the process according to any of embodiments 21) to 29) will be performed in dichloromethane.

34) According to yet another variant of embodiment 31), the reaction of the compound of formula I-2 with $TiCl_4$ in step b) of the process according to any of embodiments 21) to 29) will be performed in a mixture of toluene and dichloromethane.

35) Preferably, the reaction of the compound of formula I-2 with $TiCl_4$ in step b) of the process according to any of embodiments 21) to 34) will be performed at a temperature from 0 to 140° C.

36) More preferably, the reaction of the compound of formula I-2 with $TiCl_4$ in step b) of the process according to any of embodiments 21) to 34) will be performed at a temperature from 10 to 100° C.

37) In a particularly preferred manner, the reaction of the compound of formula I-2 with $TiCl_4$ in step b) of the process according to any of embodiments 21) to 34) will be performed at a temperature from 20 to 70° C.

38) Preferably, the reactions of steps a) and b) of the process according to embodiment 21) will both be performed in toluene.

39) In particular, the process according to embodiment 21) will comprise the following steps:

a) the reaction of the compound of formula I-1

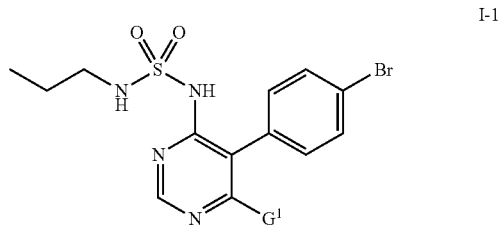

I-1 wherein G¹ represents halogen, or a salt of said compound, with 2-(tert-butoxy)ethanol in the presence of a base, in an aprotic solvent or mixture of solvents comprising dichloromethane, toluene, or a mixture of dichloromethane and toluene, at a temperature from 25 to 100° C. to obtain the compound of formula I-2

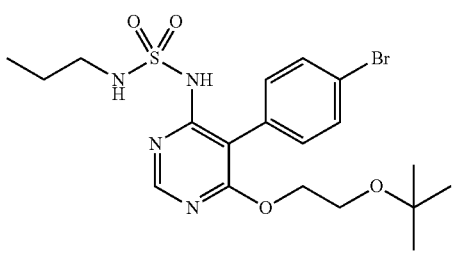

and b) the reaction of the compound of formula I-2 obtained at step a), or a salt of said compound, with TiCl$_4$, in an aprotic solvent or mixture of solvents comprising comprising dichloromethane, toluene, or a mixture of dichloromethane and toluene, at a temperature from 20 to 70° C.

40) Preferably, the reactions of steps a) and b) of the process according to embodiment 39) will both be performed in toluene.

41) According to a preferred variant of embodiments 21) to 40), the product obtained after step a) is not isolated and steps a) and b) are performed in the same reactor (that is, the 2-step process is performed as a so-called "one-pot process").

42) Preferably, the reactions of steps a) and b) of the process according to embodiment 41) will both be performed in toluene.

43) Preferably, the process according to embodiment 41) will comprise:

a) the reaction of the compound of formula I-1

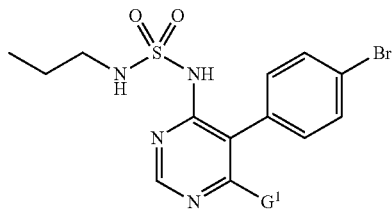

wherein G$^1$ represents halogen, or a salt of said compound, with 2-(tert-butoxy)ethanol, in dichloromethane, toluene or a mixture of toluene and dichloromethane, in the presence of a base at a temperature from 25 to 100° C. to obtain the compound of formula I-2

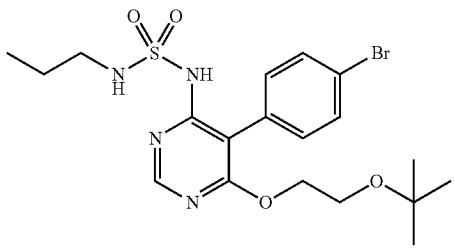

and b) the reaction of the compound of formula I-2 obtained at step a), or a salt of said compound, with TiCl$_4$ in dichloromethane, toluene or a mixture of toluene and dichloromethane at a temperature from 20 to 70° C.

44) Preferably, the base used in step a) of the process according to embodiment 43) will be selected from NaOH and potassium tert-butoxide.

45) Preferably, the reactions of steps a) and b) of the process according to embodiment 43) or 44) will both be performed in toluene.

46) More preferably, the process according to embodiment 45) will comprise:

a) the reaction of the compound of formula I-1

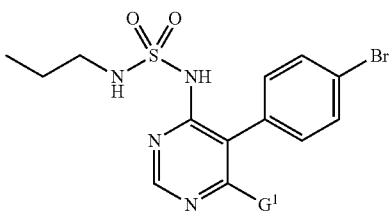

wherein G$^1$ represents halogen, or a salt of said compound, with 2-(tert-butoxy)ethanol in toluene, in the presence of NaOH or potassium tert-butoxide, at a temperature from 25 to 100° C. to obtain the compound of formula I-2

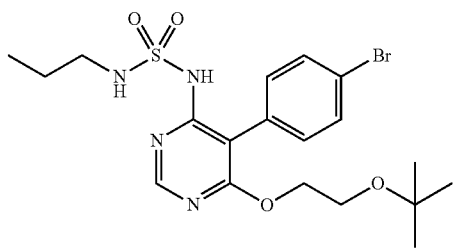

and b) the reaction of the compound of formula I-2 obtained at step a), or a salt of said compound, with TiCl$_4$ in toluene at a temperature from 20 to 70° C.

47) The invention moreover relates to the use of the compound of formula I-2 as defined in embodiment 1), or a salt thereof, in a process for manufacturing the compound of formula I-3 as defined in embodiment 12), or a salt thereof.

This invention thus notably relates to the compound, the manufacturing processes and the uses as defined in one of embodiments 1), 2), 12), 21) and 47) or to these compound, manufacturing processes and uses further limited under consideration of their respective dependencies by the characteristics of any one of embodiments 3) to 11), 13) to 20) and 22) to 46). In particular, based on the dependencies of the different embodiments as disclosed hereinabove, the following manufacturing compound, process and use embodiments are thus possible and intended and herewith specifically disclosed in individualized form:

1, 2, 3+2, 4+2, 4+3+2, 5+2, 5+3+2, 5+4+2, 5+4+3+2, 6+2, 6+3+2, 6+4+2, 6+4+3+2, 7+2, 8+2, 8+3+2, 8+4+2, 8+4+3+2, 8+7+2, 9+2, 9+3+2, 9+4+2, 9+4+3+2, 9+7+2, 10+2, 10+3+2, 10+4+2, 10+4+3+2, 10+7+2, 11+2, 12, 13+12, 14+12, 15+14+12, 16+14+12, 17+14+12, 18+12, 18+13+12, 18+14+12, 18+15+14+12, 18+16+14+12, 18+17+14+12, 19+12, 19+13+12, 19+14+12, 19+15+14+12, 19+16+14+12, 19+17+14+12, 20+12, 20+13+12, 20+14+12, 20+15+14+12, 20+16+14+12, 20+17+14+12, 21, 22+21, 23+21, 23+22+21,

24+21, 24+22+21, 24+23+21, 24+23+22+21, 25+21, 25+22+21, 25+23+21, 25+23+22+21, 26+21, 27+21, 27+22+21, 27+23+21, 27+23+22+21, 27+24+21, 27+24+22+21, 27+24+23+21, 27+24+23+22+21, 27+25+21, 27+25+22+21, 27+25+23+21, 27+25+23+22+21, 27+26+21, 28+21, 28+22+21, 28+23+21, 28+23+22+21, 28+24+21, 28+24+22+21, 28+24+23+21, 28+24+23+22+21, 28+25+21, 28+25+22+21, 28+25+23+21, 28+25+23+22+21, 28+26+21, 29+21, 30+21, 30+22+21, 30+23+21, 30+23+22+21, 30+24+21, 30+24+22+21, 30+24+23+21, 30+24+23+22+21, 30+25+21, 30+25+22+21, 30+25+23+21, 30+25+23+22+21, 30+26+21, 30+27+21, 30+27+22+21, 30+27+23+21, 30+27+23+22+21, 30+27+24+21, 30+27+24+22+21, 30+27+24+23+21, 30+27+24+23+22+21, 30+27+25+21, 30+27+25+22+21, 30+27+25+23+21, 30+27+25+23+22+21, 30+27+26+21, 30+28+21, 30+28+22+21, 30+28+23+21, 30+28+23+22+21, 30+28+24+21, 30+28+24+22+21, 30+28+24+23+21, 30+28+24+23+22+21, 30+28+25+21, 30+28+25+22+21, 30+28+25+23+21, 30+28+25+23+22+21, 30+28+26+21, 30+29+21, 31+21, 31+22+21, 31+23+21, 31+23+22+21, 31+24+21, 31+24+22+21, 31+24+23+21, 31+24+23+22+21, 31+25+21, 31+25+22+21, 31+25+23+21, 31+25+23+22+21, 31+26+21, 31+27+21, 31+27+22+21, 31+27+23+21, 31+27+23+22+21, 31+27+24+21, 31+27+24+22+21, 31+27+24+23+21, 31+27+24+23+22+21, 31+27+25+21, 31+27+25+22+21, 31+27+25+23+21, 31+27+25+23+22+21, 31+27+26+21, 31+28+21, 31+28+22+21, 31+28+23+21, 31+28+23+22+21, 31+28+24+21, 31+28+24+22+21, 31+28+24+23+21, 31+28+24+23+22+21, 31+28+25+21, 31+28+25+22+21, 31+28+25+23+21, 31+28+25+23+22+21, 31+28+26+21, 31+29+21, 32+31+21, 32+31+22+21, 32+31+23+21, 32+31+23+22+21, 32+31+24+21, 32+31+24+22+21, 32+31+24+23+21, 32+31+24+23+22+21, 32+31+25+21, 32+31+25+22+21, 32+31+25+23+21, 32+31+25+23+22+21, 32+31+26+21, 32+31+27+21, 32+31+27+22+21, 32+31+27+23+21, 32+31+27+23+22+21, 32+31+27+24+21, 32+31+27+24+22+21, 32+31+27+24+23+21, 32+31+27+24+23+22+21, 32+31+27+25+21, 32+31+27+25+22+21, 32+31+27+25+23+21, 32+31+27+25+23+22+21, 32+31+27+26+21, 32+31+28+21, 32+31+28+22+21, 32+31+28+23+21, 32+31+28+23+22+21, 32+31+28+24+21, 32+31+28+24+22+21, 32+31+28+24+23+21, 32+31+28+24+23+22+21, 32+31+28+25+21, 32+31+28+25+22+21, 32+31+28+25+23+21, 32+31+28+25+23+22+21, 32+31+28+26+21, 32+31+29+21, 33+31+21, 33+31+22+21, 33+31+23+21, 33+31+23+22+21, 33+31+24+21, 33+31+24+22+21, 33+31+24+23+21, 33+31+24+23+22+21, 33+31+25+21, 33+31+25+22+21, 33+31+25+23+21, 33+31+25+23+22+21, 33+31+26+21, 33+31+27+21, 33+31+27+22+21, 33+31+27+23+21, 33+31+27+23+22+21, 33+31+27+24+21, 33+31+27+24+22+21, 33+31+27+24+23+21, 33+31+27+24+23+22+21, 33+31+27+25+21, 33+31+27+25+22+21, 33+31+27+25+23+21, 33+31+27+25+23+22+21, 33+31+27+26+21, 33+31+28+21, 33+31+28+22+21, 33+31+28+23+21, 33+31+28+23+22+21, 33+31+28+24+21, 33+31+28+24+22+21, 33+31+28+24+23+21, 33+31+28+24+23+22+21, 33+31+28+25+21, 33+31+28+25+22+21, 33+31+28+25+23+21, 33+31+28+25+23+22+21, 33+31+28+26+21, 33+31+29+21, 34+31+21, 34+31+22+21, 34+31+23+21, 34+31+23+22+21, 34+31+24+21, 34+31+24+22+21, 34+31+24+23+21, 34+31+24+23+22+21, 34+31+25+21, 34+31+25+22+21, 34+31+25+23+21, 34+31+25+23+22+21, 34+31+26+21, 34+31+27+21, 34+31+27+22+21, 34+31+27+23+21, 34+31+27+23+22+21, 34+31+27+24+21, 34+31+27+24+22+21, 34+31+27+24+23+21, 34+31+27+24+23+22+21, 34+31+27+25+21, 34+31+27+25+22+21, 34+31+27+25+23+21, 34+31+27+25+23+22+21, 34+31+27+26+21, 34+31+28+21, 34+31+28+22+21, 34+31+28+23+21, 34+31+28+23+22+21, 34+31+28+24+21, 34+31+28+24+22+21, 34+31+28+24+23+21, 34+31+28+24+23+22+21, 34+31+28+25+21, 34+31+28+25+22+21, 34+31+28+25+23+21, 34+31+28+25+23+22+21, 34+31+28+26+21, 34+31+29+21, 35+21, 35+22+21, 35+26+21, 35+29+21, 35+31+21, 35+31+22+21, 35+31+23+21, 35+31+23+22+21, 35+31+24+21, 35+31+24+22+21, 35+31+24+23+21, 35+31+24+23+22+21, 35+31+25+21, 35+31+25+22+21, 35+31+25+23+21, 35+31+25+23+22+21, 35+31+26+21, 35+31+27+21, 35+31+27+22+21, 35+31+27+23+21, 35+31+27+24+21, 35+31+27+24+22+21, 35+31+27+24+23+21, 35+31+27+24+23+22+21, 35+31+27+25+21, 35+31+27+25+22+21, 35+31+27+25+23+21, 35+31+27+25+23+22+21, 35+31+27+26+21, 35+31+28+21, 35+31+28+22+21, 35+31+28+23+21, 35+31+28+23+22+21, 35+31+28+24+21, 35+31+28+24+22+21, 35+31+28+24+23+21, 35+31+28+24+23+22+21, 35+31+28+25+21, 35+31+28+25+22+21, 35+31+28+25+23+21, 35+31+28+25+23+22+21, 35+31+28+26+21, 35+31+29+21, 36+21, 36+22+21, 36+26+21, 36+29+21, 36+31+21, 36+31+22+21, 36+31+23+21, 36+31+23+22+21, 36+31+24+21, 36+31+24+22+21, 36+31+24+23+21, 36+31+24+23+22+21, 36+31+25+21, 36+31+25+22+21, 36+31+25+23+21, 36+31+25+23+22+21, 36+31+26+21, 36+31+27+21, 36+31+27+22+21, 36+31+27+23+21, 36+31+27+23+22+21, 36+31+27+24+21, 36+31+27+24+22+21, 36+31+27+24+23+21, 36+31+27+24+23+22+21, 36+31+27+25+21, 36+31+27+25+22+21, 36+31+27+25+23+21, 36+31+27+25+23+22+21, 36+31+27+26+21, 36+31+28+21, 36+31+28+22+21, 36+31+28+23+21, 36+31+28+23+22+21, 36+31+28+24+21, 36+31+28+24+22+21, 36+31+28+24+23+21, 36+31+28+24+23+22+21, 36+31+28+25+21, 36+31+28+25+22+21, 36+31+28+25+23+21, 36+31+28+25+23+22+21, 36+31+28+26+21, 36+31+29+21, 37+21, 37+22+21, 37+26+21, 37+29+21, 37+31+21, 37+31+22+21, 37+31+23+21, 37+31+23+22+21, 37+31+24+21, 37+31+24+22+21, 37+31+24+23+21, 37+31+24+23+22+21, 37+31+25+21, 37+31+25+22+21, 37+31+25+23+21, 37+31+25+23+22+21, 37+31+26+21, 37+31+27+21, 37+31+27+22+21, 37+31+27+23+21, 37+31+27+23+22+21, 37+31+27+24+21, 37+31+27+24+22+21, 37+31+27+24+23+21, 37+31+27+24+23+22+21, 37+31+27+25+21, 37+31+27+25+22+21, 37+31+27+25+23+21, 37+31+27+25+23+22+21, 37+31+27+26+21,

37+31+28+21, 37+31+28+22+21, 37+31+28+23+21, 37+31+28+23+22+21, 37+31+28+24+21, 37+31+28+24+22+21, 37+31+28+24+23+21, 37+31+28+24+23+22+21, 37+31+28+25+21, 37+31+28+25+22+21, 37+31+28+25+23+21, 37+31+28+25+23+22+21, 37+31+28+26+21, 37+31+29+21, 38+21, 39+21, 40+39+21, 41+21, 41+22+21, 41+26+21, 41+29+21, 41+31+21, 41+31+22+21, 41+31+23+21, 41+31+23+22+21, 41+31+24+21, 41+31+24+22+21, 41+31+24+23+21, 41+31+24+23+22+21, 41+31+25+21, 41+31+25+22+21, 41+31+25+23+21, 41+31+25+23+22+21, 41+31+26+21, 41+31+27+21, 41+31+27+22+21, 41+31+27+23+21, 41+31+27+23+22+21, 41+31+27+24+21, 41+31+27+24+22+21, 41+31+27+24+23+21, 41+31+27+24+23+22+21, 41+31+27+25+21, 41+31+27+25+22+21, 41+31+27+25+23+21, 41+31+27+25+23+22+21, 41+31+27+26+21, 41+31+28+21, 41+31+28+22+21, 41+31+28+23+21, 41+31+28+23+22+21, 41+31+28+24+21, 41+31+28+24+22+21, 41+31+28+24+23+21, 41+31+28+24+23+22+21, 41+31+28+25+21, 41+31+28+25+22+21, 41+31+28+25+23+21, 41+31+28+25+23+22+21, 41+31+28+26+21, 41+31+29+21, 41+38+21, 41+39+21, 41+40+39+21, 42+41+21, 42+41+22+21, 42+41+26+21, 42+41+29+21, 42+41+31+21, 42+41+31+22+21, 42+41+31+23+21, 42+41+31+23+22+21, 42+41+31+24+21, 42+41+31+24+22+21, 42+41+31+24+23+21, 42+41+31+24+23+22+21, 42+41+31+25+21, 42+41+31+25+22+21, 42+41+31+25+23+21, 42+41+31+25+23+22+21, 42+41+31+26+21, 42+41+31+27+21, 42+41+31+27+22+21, 42+41+31+27+23+21, 42+41+31+27+23+22+21, 42+41+31+27+24+21, 42+41+31+27+24+22+21, 42+41+31+27+24+23+21, 42+41+31+27+24+23+22+21, 42+41+31+27+25+21, 42+41+31+27+25+22+21, 42+41+31+27+25+23+21, 42+41+31+27+25+23+22+21, 42+41+31+27+26+21, 42+41+31+28+21, 42+41+31+28+22+21, 42+41+31+28+23+21, 42+41+31+28+23+22+21, 42+41+31+28+24+21, 42+41+31+28+24+22+21, 42+41+31+28+24+23+21, 42+41+31+28+24+23+22+21, 42+41+31+28+25+21, 42+41+31+28+25+22+21, 42+41+31+28+25+23+21, 42+41+31+28+25+23+22+21, 42+41+31+28+26+21, 42+41+31+29+21, 42+41+38+21, 42+41+39+21, 42+41+40+39+21, 43+41+21, 43+41+22+21, 43+41+26+21, 43+41+29+21, 43+41+31+21, 43+41+31+22+21, 43+41+31+23+21, 43+41+31+23+22+21, 43+41+31+24+21, 43+41+31+24+22+21, 43+41+31+24+23+21, 43+41+31+24+23+22+21, 43+41+31+25+21, 43+41+31+25+22+21, 43+41+31+25+23+21, 43+41+31+25+23+22+21, 43+41+31+26+21, 43+41+31+27+21, 43+41+31+27+22+21, 43+41+31+27+23+21, 43+41+31+27+23+22+21, 43+41+31+27+24+21, 43+41+31+27+24+22+21, 43+41+31+27+24+23+21, 43+41+31+27+24+23+22+21, 43+41+31+27+25+21, 43+41+31+27+25+22+21, 43+41+31+27+25+23+21, 43+41+31+27+25+23+22+21, 43+41+31+27+26+21, 43+41+31+28+21, 43+41+31+28+22+21, 43+41+31+28+23+21, 43+41+31+28+23+22+21, 43+41+31+28+24+21, 43+41+31+28+24+22+21, 43+41+31+28+24+23+21, 43+41+31+28+24+23+22+21, 43+41+31+28+25+21, 43+41+31+28+25+22+21, 43+41+31+28+25+23+21, 43+41+31+28+25+23+22+21, 43+41+31+28+26+21, 43+41+31+29+21, 43+41+38+21, 43+41+39+21, 43+41+40+39+21, 44+43+41+21, 44+43+41+22+21, 44+43+41+26+21, 44+43+41+29+21, 44+43+41+31+21, 44+43+41+31+22+21, 44+43+41+31+23+21, 44+43+41+31+23+22+21, 44+43+41+31+24+21, 44+43+41+31+24+22+21, 44+43+41+31+24+23+21, 44+43+41+31+24+23+22+21, 44+43+41+31+25+21, 44+43+41+31+25+22+21, 44+43+41+31+25+23+21, 44+43+41+31+25+23+22+21, 44+43+41+31+26+21, 44+43+41+31+27+21, 44+43+41+31+27+22+21, 44+43+41+31+27+23+21, 44+43+41+31+27+23+22+21, 44+43+41+31+27+24+21, 44+43+41+31+27+24+22+21, 44+43+41+31+27+24+23+21, 44+43+41+31+27+24+23+22+21, 44+43+41+31+27+25+21, 44+43+41+31+27+25+22+21, 44+43+41+31+27+25+23+21, 44+43+41+31+27+25+23+22+21, 44+43+41+31+27+26+21, 44+43+41+31+28+21, 44+43+41+31+28+22+21, 44+43+41+31+28+23+21, 44+43+41+31+28+23+22+21, 44+43+41+31+28+24+21, 44+43+41+31+28+24+22+21, 44+43+41+31+28+24+23+21, 44+43+41+31+28+24+23+22+21, 44+43+41+31+28+25+21, 44+43+41+31+28+25+22+21, 44+43+41+31+28+25+23+21, 44+43+41+31+28+25+23+22+21, 44+43+41+31+28+26+21, 44+43+41+31+29+21, 44+43+41+38+21, 44+43+41+39+21, 44+43+41+40+39+21, 45+43+41+21, 45+43+41+22+21, 45+43+41+26+21, 45+43+41+29+21, 45+43+41+31+21, 45+43+41+31+22+21, 45+43+41+31+23+21, 45+43+41+31+23+22+21, 45+43+41+31+24+21, 45+43+41+31+24+22+21, 45+43+41+31+24+23+21, 45+43+41+31+24+23+22+21, 45+43+41+31+25+21, 45+43+41+31+25+22+21, 45+43+41+31+25+23+21, 45+43+41+31+25+23+22+21, 45+43+41+31+26+21, 45+43+41+31+27+21, 45+43+41+31+27+22+21, 45+43+41+31+27+23+21, 45+43+41+31+27+23+22+21, 45+43+41+31+27+24+21, 45+43+41+31+27+24+22+21, 45+43+41+31+27+24+23+21, 45+43+41+31+27+24+23+22+21, 45+43+41+31+27+25+21, 45+43+41+31+27+25+22+21, 45+43+41+31+27+25+23+21, 45+43+41+31+27+25+23+22+21, 45+43+41+31+27+26+21, 45+43+41+31+28+21, 45+43+41+31+28+22+21, 45+43+41+31+28+23+21, 45+43+41+31+28+23+22+21, 45+43+41+31+28+24+21, 45+43+41+31+28+24+22+21, 45+43+41+31+28+24+23+21, 45+43+41+31+28+24+23+22+21, 45+43+41+31+28+25+21, 45+43+41+31+28+25+22+21, 45+43+41+31+28+25+23+21, 45+43+41+31+28+25+23+22+21, 45+43+41+31+28+26+21, 45+43+41+31+29+21, 45+43+41+38+21, 45+43+41+39+21, 45+43+41+40+39+21, 45+44+43+41+21, 45+44+43+41+22+21, 45+44+43+41+26+21, 45+44+43+41+29+21, 45+44+43+41+31+21, 45+44+43+41+31+22+21, 45+44+43+41+31+23+21, 45+44+43+41+31+23+22+21, 45+44+43+41+31+24+21, 45+44+43+41+31+24+22+21, 45+44+43+41+31+24+23+21, 45+44+43+41+31+24+23+22+21, 45+44+43+41+31+25+21, 45+44+43+41+31+25+22+21, 45+44+43+41+31+25+23+21, 45+44+43+41+31+25+23+22+21, 45+44+43+41+31+26+21, 45+44+43+41+31+27+21,

45+44+43+41+31+27+22+21,
45+44+43+41+31+27+23+21,
45+44+43+41+31+27+23+22+21,
45+44+43+41+31+27+24+21,
45+44+43+41+31+27+24+22+21,
45+44+43+41+31+27+24+23+21,
45+44+43+41+31+27+24+23+22+21,
45+44+43+41+31+27+25+21,
45+44+43+41+31+27+25+22+21,
45+44+43+41+31+27+25+23+21,
45+44+43+41+31+27+25+23+22+21,
45+44+43+41+31+27+26+21, 45+44+43+41+31+28+21,
45+44+43+41+31+28+22+21,
45+44+43+41+31+28+23+21,
45+44+43+41+31+28+23+22+21,
45+44+43+41+31+28+24+21,
45+44+43+41+31+28+24+22+21,
45+44+43+41+31+28+24+23+21,
45+44+43+41+31+28+24+23+22+21,
45+44+43+41+31+28+25+21,
45+44+43+41+31+28+25+22+21,
45+44+43+41+31+28+25+23+21,
45+44+43+41+31+28+25+23+22+21,
45+44+43+41+31+28+26+21, 45+44+43+41+31+29+21,
45+44+43+41+38+21, 45+44+43+41+39+21,
45+44+43+41+40+39+21, 46+45+43+41+21,
46+45+43+41+22+21, 46+45+43+41+26+21,
46+45+43+41+29+21, 46+45+43+41+31+21,
46+45+43+41+31+22+21, 46+45+43+41+31+23+21,
46+45+43+41+31+23+22+21, 46+45+43+41+31+24+21,
46+45+43+41+31+24+22+21,
46+45+43+41+31+24+23+21,
46+45+43+41+31+24+23+22+21,
46+45+43+41+31+25+21, 46+45+43+41+31+25+22+21,
46+45+43+41+31+25+23+21,
46+45+43+41+31+25+23+22+21,
46+45+43+41+31+26+21, 46+45+43+41+31+27+21,
46+45+43+41+31+27+22+21,
46+45+43+41+31+27+23+21,
46+45+43+41+31+27+23+22+21,
46+45+43+41+31+27+24+21,
46+45+43+41+31+27+24+22+21,
46+45+43+41+31+27+24+23+21,
46+45+43+41+31+27+24+23+22+21,
46+45+43+41+31+27+25+21,
46+45+43+41+31+27+25+22+21,
46+45+43+41+31+27+25+23+21,
46+45+43+41+31+27+25+23+22+21,
46+45+43+41+31+27+26+21, 46+45+43+41+31+28+21,
46+45+43+41+31+28+22+21,
46+45+43+41+31+28+23+21,
46+45+43+41+31+28+23+22+21,
46+45+43+41+31+28+24+21,
46+45+43+41+31+28+24+22+21,
46+45+43+41+31+28+24+23+21,
46+45+43+41+31+28+24+23+22+21,
46+45+43+41+31+28+25+21,
46+45+43+41+31+28+25+22+21,
46+45+43+41+31+28+25+23+21,
46+45+43+41+31+28+25+23+22+21,
46+45+43+41+31+28+26+21, 46+45+43+41+31+29+21,
46+45+43+41+38+21, 46+45+43+41+39+21,
46+45+43+41+40+39+21, 46+45+43+41+41+21,
46+45+44+43+41+22+21, 46+45+44+43+41+26+21,
46+45+44+43+41+29+21, 46+45+44+43+41+31+21,
46+45+44+43+41+31+22+21,
46+45+44+43+41+31+23+21,
46+45+44+43+41+31+23+22+21,
46+45+44+43+41+31+24+21,
46+45+44+43+41+31+24+22+21,
46+45+44+43+41+31+24+23+21,
46+45+44+43+41+31+24+23+22+21,
46+45+44+43+41+31+25+21,
46+45+44+43+41+31+25+22+21,
46+45+44+43+41+31+25+23+21,
46+45+44+43+41+31+25+23+22+21,
46+45+44+43+41+31+26+21,
46+45+44+43+41+31+27+21,
46+45+44+43+41+31+27+22+21,
46+45+44+43+41+31+27+23+21,
46+45+44+43+41+31+27+23+22+21,
46+45+44+43+41+31+27+24+21,
46+45+44+43+41+31+27+24+22+21,
46+45+44+43+41+31+27+24+23+21,
46+45+44+43+41+31+27+24+23+22+21,
46+45+44+43+41+31+27+25+21,
46+45+44+43+41+31+27+25+22+21,
46+45+44+43+41+31+27+25+23+21,
46+45+44+43+41+31+27+25+23+22+21,
46+45+44+43+41+31+27+26+21,
46+45+44+43+41+31+28+21,
46+45+44+43+41+31+28+22+21,
46+45+44+43+41+31+28+23+21,
46+45+44+43+41+31+28+23+22+21,
46+45+44+43+41+31+28+24+21,
46+45+44+43+41+31+28+24+22+21,
46+45+44+43+41+31+28+24+23+21,
46+45+44+43+41+31+28+24+23+22+21,
46+45+44+43+41+31+28+25+21,
46+45+44+43+41+31+28+25+22+21,
46+45+44+43+41+31+28+25+23+21,
46+45+44+43+41+31+28+25+23+22+21,
46+45+44+43+41+31+28+26+21,
46+45+44+43+41+31+29+21, 46+45+44+43+41+38+21,
46+45+44+43+41+39+21, 46+45+44+43+41+40+39+21
and 47.

In the list above, the numbers refer to the embodiments according to their numbering provided hereinabove whereas "+" indicates the dependency from another embodiment. The different individualised embodiments are separated by commas. In other words, "5+3+2" for example refers to embodiment 5) depending on embodiment 3), depending on embodiment 2), i.e. embodiment "5+3+2" corresponds to embodiment 2) further limited by the features of embodiments 3) and 5). Likewise, "19+15+14+12" refers to embodiment 19) depending mutatis mutandis on embodiments 15) and 14), depending on embodiment 12), i.e. embodiment "19+15+14+12" corresponds to embodiment 12) further limited by the features of embodiment 14), further limited by the features of embodiments 15) and 19).

Methods for preparing the starting compound, i.e. the compound of formula I-1 as defined in embodiment 2), are described in the section "Preparation of starting materials" hereafter, while methods for obtaining macitentan from the compound of formula I-3 as defined in embodiment 12) are described in the section "Use of the compound of formula I-3" hereafter.

Preparation of Starting Materials

The preparation of the compound of formula I-1 as defined in embodiment 2) can be performed as described in WO 02/053557 or in Bolli et al., *J. Med. Chem.* (2012), 55, 7849-7861.

In particular, the compound of formula I-1 can be prepared as described in the section "EXAMPLES" (see subsection "Preparations").

Use of the Compound of Formula 1-3

The preparation of macitentan starting from the compound of formula I-3 as defined in embodiment 12) can be performed as described in WO 02/053557 or in Bolli et al., *J. Med. Chem.* (2012), 55, 7849-7861. In case the compound of formula I-3 is obtained according to the one pot process according to any of embodiments 39) to 43) described above, the one pot process may advantageously be pursued by the addition of a base like KOtBu and of 5-bromo-2-chloropyrimidine to directly obtain macitentan.

In particular, macitentan can be prepared starting from the compound of formula I-3 as described in the section "EXAMPLES" (see subsection "Preparations").

ABBREVIATIONS AND TERMS USED IN THIS TEXT

Abbreviations:

The following abbreviations are used throughout the specification and the examples:

Ac acetyl
approx. approximately
aq. aqueous
CHex cyclohexane
DCM dichloromethane
DMAC dimethylacetamide
DME 1,2-dimethoxyethane
DMF dimethylformamide
DMSO dimethylsulfoxide
d6-DMSO perdeuterated dimethylsulfoxide
EA ethyl acetate
eq. equivalent(s)
Hept heptane
Hex hexane
iPrOH isopropanol
iPrOAc isopropyl acetate
LC-MS liquid chromatography-mass spectroscopy
MS mass spectroscopy
MeCHex methylcyclohexane
MeCN acetonitrile
MeOH methanol
NMP N-methylpyrrolidone
org. organic
Pd/C palladium on carbon
% a/a percent determined by area ratio
rt room temperature
TBME tert-butyl methyl ether
TFA trifluoroacetic acid
THF tetrahydrofurane
TMSI trimethylsilyl iodide
TMSCl trimethylsilyl chloride
$t_R$ retention time Definitions of Particular Terms Used in this Text:

The following paragraphs provide definitions of the various chemical moieties for the compounds according to the invention as well as other particular terms used in this text and are intended to apply uniformly throughout the specification and claims, unless an otherwise expressly set out definition provides a broader or narrower definition:

The term "halogen" refers to fluorine, chlorine, bromine or iodine, and preferably to fluorine or chlorine.

The expression "aprotic solvent" refers to a solvent which does not have an acidic hydrogen. Representative examples of aprotic solvents include DCM, MeCN, EA, iPrOAc, THF, 2-methyl-tetrahydrofurane, DMAC, DME, DMF, DMSO, dioxane, diethyl ether, NMP, TBME, cyclopentyl methyl ether, toluene, xylenes, Hex, Hept, CHex and MeCHex.

The expression "mixture of aprotic solvents" refers to a mixture of aprotic solvents as previously defined. Representative examples of mixtures of aprotic solvents include, but are not limited to: a mixture of two solvents selected from the group consisting of DCM, MeCN, EA, iPrOAc, THF, 2-methyl-tetrahydrofurane, DMAC, DME, DMF, DMSO, dioxane, diethyl ether, NMP, TBME, cyclopentyl methyl ether, toluene, xylenes, Hex, Hept, CHex and MeCHex; or a mixture of toluene, DCM and a solvent selected from MeCN, EA, iPrOAc, THF, 2-methyl-tetrahydrofurane, DMAC, DME, DMF, DMSO, dioxane, diethyl ether, NMP, TBME, cyclopentyl methyl ether, Hex, Hept, CHex and MeCHex.

The expression "room temperature" as used herein refers to a temperature of from 20 to 30° C., and preferably 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Particular embodiments of the invention are described in the following Examples, which serve to illustrate the invention in more detail without limiting its scope in any way.

EXAMPLES

All temperatures given are external temperatures and are stated in ° C. Compounds were characterized by $^1$H-NMR (400 MHz) or $^{13}$C-NMR (100 MHz) (Bruker; chemical shifts δ are given in ppm relative to the solvent used; multiplicities: s=singlet, d=doublet, t=triplet; p=pentuplet, hex=hextet, hept=heptet, m=multiplet, br.=broad, coupling constants are given in Hz); by LC-MS (Agilent MS detector G1956B with Agilent 1200 Binary Pump and DAD).

Parameters of the LC-MS Method:

| | |
|---|---|
| Injection volume: | 2 μL |
| Column: | Kinetex C18, 2.6 μm, 2.1 × 50 mm |
| Column flow rate: | 1 mL/min |
| Eluents: | Eluent A: water + 0.08% TFA |
| | Eluent B: MeCN + 0.012% TFA |
| Gradient: | 2.0 min 95% B |
| | 2.8 min 95% B |
| | 3.0 min 5% B |
| Temperature: | 40° C. |
| Detector wavelength | 210 nm |

Preparation A

N-(5-(4-bromophenyl)-6-chloropyrimidin-4-yl)propane-1-sulfamide

A.i. Propane-1-sulfamide

Chlorosulfonyl isocyanate (12.3 mL; 0.14 mol; 1.0 eq.) was slowly added to a cold (−35° C.) solution of benzyl alcohol (14.7 mL; 0.14 mol; 1.0 eq.) in DCM (130 mL) over 30 min. A solution of n-propylamine (14 mL, 0.17 mol; 1.2 eq.) and triethylamine (29.5 mL; 0.21 mol; 1.5 eq.) in DCM (35 mL) was slowly added dropwise at −50° C. The mixture was warmed to 20° C. for 2 h. It was washed with water, followed by aq. 33% HCl and water. The mixture was warmed to 30° C. and the layers were separated. The org. phase was washed with a mixture of Et₃N (20 mL; 0.14 mol; 1 eq.) and water (50 mL) so that pH>5. THF (85 mL) was added followed by 10% Pd/C (1 g). The reaction mixture was hydrogenated at 25° C. for 6 h under 6 bars of hydrogen. It was filtered over Celite. The volatiles were removed. DMSO (120 mL) was added. The solution of propane-1-sulfamide (100% theoretical yield) thus obtained in DMSO was used as such in the next step.

A.ii. N-(5-(4-bromophenyl)-6-chloropyrimidin-4-yl)propane-1-sulfamide tBuOK (16.0 g; 0.14 mol; 1 eq.) was added to the above prepared cold (5° C.) solution of Intermediate A.i in DMSO. The resulting suspension was heated to 20° C. and stirred for 30 min. 5-(4-bromophenyl)-4,6-dichloropyrimidine (10.7 g; 0.035 mol; 0.25 eq.) was added portionwise and the mixture was heated to 50° C. for 1 h. Water was added. The pH of the solution was adjusted to 4-5 using 33% aq. HCl. The suspension was cooled to 0° C. and stirred for 30 min. It was filtered off, rinsed with a solution of water and MeOH and dried under reduced pressure to yield the title compound as a white solid (12.6 g, 89% yield with respect to 5-(4-bromophenyl)-4,6-dichloropyrimidine).

Preparation B

N-[5-(4-bromophenyl)-6-[2-[(5-bromo-2-pyrimidinyl)oxy]ethoxy]-4-pyrimidinyl]-N'-propylsulfamide (macitentan)

N-(5-(4-bromophenyl)-6-(2-hydroxyethoxy)pyrimidin-4-yl)propane-1-sulfamide (200 g; 0.46 mol; see Example 2 or 3) and 5-bromo-2-chloropyrimidine (117 g; 0.60 mol; 1.3 eq) were dissolved in toluene (3 L) and DMF (400 mL). The reaction mixture was warmed up to 50° C. and toluene (approx. 400 mL) was distilled our under reduced pressure. The mixture was cooled to 0° C. and tBuOK (156 g, 3 eq, 1.38 mol) was added portionwise. It was stirred at 20° C. for 1 h. Water (1 L) was added and the pH of the solution was adjusted to 3-5 using 33% aq. HCl. The mixture was heated to 50° C. and the layers were separated. The org. phase was treated with charcoal at 50° C. and filtered over Celite. The filter cake was rinsed with toluene. At 50° C., water (1 L) was added to the org. layer. The layers were separated. The org. layer was concentrated under reduced pressure to a total volume of 1 L and cooled to 0° C. The solid obtained was filtered off. It was rinsed with toluene and MeOH. The crude material was suspended in EA (1 L) and heated to 50° C. 300 mL of EA were distilled out and MeOH (400 mL) was added. The suspension was cooled down to 0° C. The solid was filtered off, rinsed with MeOH and dried under reduced pressure to afford the title compound as a white solid (225 g; 83% yield).

Example 1

N-(5-(4-bromophenyl)-6-(2-(tert-butoxy)ethoxy)pyrimidin-4-yl)propane-1-sulfamide:

Variant 1:
2-(tert-butoxy)ethanol (38.9 mL, 296 mol, 6.0 eq.) and powdered NaOH (7.9 g, 197 mmol, 4.0 eq.) were added to a suspension of N-(5-(4-bromophenyl)-6-chloropyrimidin-4-yl)propane-1-sulfamide (20 g, 1.0 eq.; see Preparation A) in toluene (200 mL). The reaction mixture was heated to reflux for 5 h. It was cooled to rt and water (200 mL) was added. After addition of 25% aq. HCl to reach pH 2-4, the org. layer was separated, washed twice with water (200 mL) and concentrated to dryness. The crude expected product was obtained as a brown oil that solidified upon standing overnight (20.6 g; 86% yield; purity: 85% a/a LC). This material was used as such without further purification. An analytically pure sample was prepared by recrystallization from iPrOAc/Hept.

¹H-NMR (d6-DMSO) δ: 9.82 (s, 1H); 8.48 (s, 1H); 7.62 (d, J=8.4 Hz, 2H); 7.24 (d, J=8.4 Hz, 3H); 4.33-4.30 (m, 2H); 3.51-3.48 (m, 2H); 2.82-2.77 (m, 2H); 1.42 (hept, J=7.4 Hz, 2H); 1.03 (s, 9H); 0.80 (t, J=7.4 Hz, 3H).

LC-MS: $t_R$=1.77 min; [M+1]⁺=487 and 489.

Variant 2:
N-(5-(4-bromophenyl)-6-chloropyrimidin-4-yl)propane-1-sulfamide (1000 g, 2.30 mol; see Preparation A) and powdered NaOH (394 g, 9.9 mol, 4.0 eq.) were charged into a 30 L Büchi reactor. Toluene (10 L) was added. The resulting suspension was stirred at 20° C. for 5 min. 2-(tert-butoxy)ethanol (1.95 L, 14.8 mol, 6.0 eq.) was added dropwise. After completion of the addition, the reaction mixture was heated to 85° C. for 16 h. The mixture was cooled down to 20° C. Water (10 L) was added, followed by the addition of 25% aq. HCl (1.5 L, 12.3 mol, 5 eq.). The layers were separated. The org. phase was washed with water (10 L). This operation was repeated twice. The org. phase was concentrated to dryness under reduced pressure (50° C., 100 mbar) to afford the expected product as a crude brown oil that solidified upon standing overnight (1038 g; 86% yield; purity (LC-MS): 90% a/a). This material was used as such in the next step without further purification. The product had NMR data equivalent to those obtained for the product of Variant 1.

Variant 3:
N-(5-(4-bromophenyl)-6-chloropyrimidin-4-yl)propane-1-sulfamide (35 g, 86 mmol; see Preparation A) and KOtBu (38.7 g, 0.35 mol, 4.0 eq.) were charged into a round-bottom flask. Toluene (350 mL) was added. The resulting suspension was stirred at 20° C. for 5 min. 2-(tert-butoxy)ethanol (34.0 mL, 0.26 mol, 3.0 eq.) was added dropwise. After completion of the addition, the reaction mixture was heated to 85° C. for 2 h. The mixture was cooled down to 20° C. Water (0.5 L) was added, followed by the addition of 10% aq. citric acid (0.5 L). The layers were separated. The org. phase was washed with brine 3 times (0.5 L each) and concentrated to dryness to afford the crude expected product as a brown oil (37.8 g, 90% yield).

The product had NMR data equivalent to those obtained for the product of Variant 1.

Example 2

N-(5-(4-bromophenyl)-6-(2-hydroxyethoxy)pyrimidin-4-yl)propane-1-sulfamide

Variant 1:
A solution of the crude compound of Example 1 (100 g; 0.20 mol; obtained according to Example 1, Variant 2) in DCM (1 L) was cooled to 0° C. A 1M solution of TiCl₄ in DCM (309 mL; 309 mmol; 1.5 eq.) was added dropwise. After completion of the addition, the reaction mixture was stirred for 15 h at 20° C. Water (1 L) was added. The layers were separated. The org. layer was concentrated to about 500 mL. Water was added (400 mL) and the remaining amount of DCM was removed by distillation. MeOH (200 mL) was added and the resulting suspension was stirred vigorously for 1 h. The solid was filtered off and rinsed with cold water and cold methanol. It was dried under vacuum to afford the title compound as a beige solid (86 g; 97% yield).

The product had NMR data equivalent to those reported in Bolli et al., *J. Med. Chem.* (2012), 55, 7849-7861.

LC-MS: $t_R$=1.46 min; [M+1]$^+$=431 and 433.

Variant 2:

A solution of the crude compound of Example 1 (2 g, 4.1 mmol; obtained according to Example 1, Variant 1) in toluene (20 mL) was cooled to 0° C. A 1M solution of TiCl$_4$ in toluene (6.15 mL, 6.15 mmol, 1.5 eq.) was added dropwise. After completion of the addition, the reaction mixture was stirred for 15 h at 20° C. At this time, a 1M solution of TiCl$_4$ in toluene (1.0 mL, 1.0 mmol, 0.25 eq.) was added dropwise. After 4 h, water was added. The resulting suspension was vigorously stirred for 4 h. It was filtered off and rinsed with iPrOH to afford the title compound as a white solid (1.5 g; 85% yield).

The product had NMR data equivalent to those reported in Bolli et al., *J. Med. Chem.* (2012), 55, 7849-7861.

Example 3

N-(5-(4-bromophenyl)-6-(2-hydroxyethoxy)pyrimidin-4-yl)propane-1-sulfamide (One Pot Preparation)

N-(5-(4-bromophenyl)-6-chloropyrimidin-4-yl)propane-1-sulfamide (100 g; 0.246 mol; see Preparation A) and KOtBu (110 g; 0.99 mol; 4.0 eq.) were charged into a 2 L reactor. Toluene (1 L) was added. The resulting suspension was stirred at 20° C. for 5 min. 2-(tert-butoxy)ethanol (97 mL; 0.74 mol; 3.0 eq.) was added dropwise. After completion of the addition, the reaction mixture was heated to 85° C. for 2 h. After completion of the reaction, the mixture was cooled down to 20° C. Water (0.5 L) was added, followed by the addition of 10% aq. citric acid (0.5 L). The layers were separated. The org. phase was washed with brine 3 times (0.5 L each) and azeotropically dried with toluene (1 L) to a volume of approx. 1 L. The reaction mixture was heated to 50° C. A 1M solution of TiCl$_4$ in toluene (420 mL, 0.42 mol; 1.7 eq.) was added dropwise with vigorous stirring. After completion of the addition, it was stirred at 35° C. for 20 h. Water (0.75 L) was added and the resulting beige suspension was stirred for 15 h. It was filtered off, rinsed with toluene (300 mL) and dried to afford the title compound as a white solid (91 g; 86% yield; purity (LC-MS): 100% a/a).

The product had NMR data equivalent to those reported in Bolli et al., *J. Med. Chem.* (2012), 55, 7849-7861.

The invention claimed is:

1. The compound of formula I-2

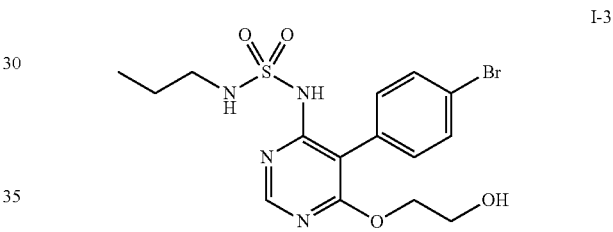

or a salt thereof.

2. A process for manufacturing the compound of formula I-2 as defined in claim 1, said process comprising the reaction of the compound of formula I-1

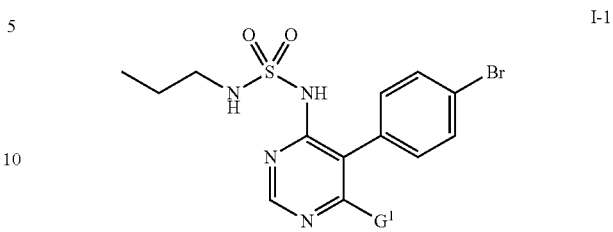

wherein G$^1$ represents halogen, or a salt of said compound, with 2-(tert-butoxy)ethanol in the presence of a base at a temperature from 25 to 140° C.

3. A process according to claim 2, wherein the compound of formula I-1 is such that G$^1$ represents chlorine.

4. A process according to claim 2, wherein the base is selected from the group consisting of NaOH, KOH and potassium tert-butylate.

5. A process according to claim 2, which is performed in an aprotic solvent or mixture of solvents comprising dichloromethane, toluene, or a mixture of dichloromethane and toluene.

6. A process for manufacturing the compound of formula I-3

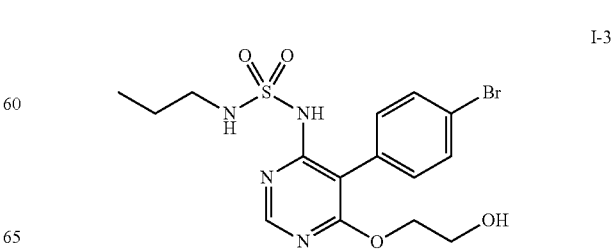

or a salt thereof, said process comprising the reaction of the compound of formula I-2 as defined in claim 1, or a salt of said compound, with TiCl$_4$ in an aprotic solvent or mixture of aprotic solvents.

7. A process according to claim 6, wherein the aprotic solvent or mixture of aprotic solvents comprises toluene, dichloromethane or a mixture of toluene and dichloromethane.

8. A process according to claim 6, wherein the reaction of the compound of formula I-2 with TiCl$_4$ is performed in toluene.

9. A process according to claim 6, wherein the reaction of the compound of formula I-2 with TiCl$_4$ is performed at a temperature from 10 to 100° C.

10. A process according to claim 9, wherein the reaction of the compound of formula I-2 with TiCl$_4$ is performed at a temperature from 20 to 70° C.

11. A process for manufacturing the compound of formula I-3 or a salt thereof, said process comprising:
a) the reaction of the compound of formula I-1

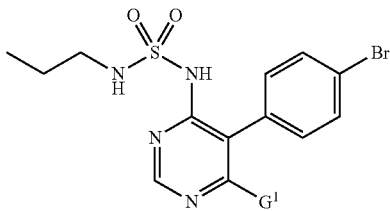

I-1 wherein $G^1$ represents halogen, or a salt of said compound, with 2-(tert-butoxy)ethanol in the presence of a base at a temperature from 25 to 140° C. to obtain the compound of formula I-2 as defined in claim 1, or a salt of said compound, and b) the reaction of the compound or salt obtained at step a) with $TiCl_4$ in an aprotic solvent or mixture of solvents.

12. A process according to claim 11, wherein the compound of formula I-1 is such that $G^1$ represents chlorine.

13. A process according to claim 11, wherein the reactions of steps a) and b) of the process according to claim 11 are both performed in toluene.

14. A process according to claim 11, wherein the product obtained after step a) is not isolated and steps a) and b) are performed in the same reactor.

15. A process for manufacturing macitentan comprising
   manufacturing a compound of formula I-3 in accordance with the process of claim 11,
   reacting the compound of formula I-3 with 5-bromo-2-chloropyrimidine, and
   recovering the macitentan thus obtained.

* * * * *